United States Patent [19]

Arcuri et al.

[11] Patent Number: 5,223,418

[45] Date of Patent: Jun. 29, 1993

[54] **METHOD OF IMPROVING THE YIELD OF HETEROLOGOUS PROTEINS PRODUCED BY *STREPTOMYCES LIVIDANS***

[75] Inventors: Edward J. Arcuri, Kimberton; Mary E. Brawner, Wayne; Mary J. Donovan, St. Davids; Robert G. Gerber, Worcester; John A. Keller, King of Prussia, all of Pa.

[73] Assignee: SmithKline Beecham Corporation, Philadelphia, Pa.

[21] Appl. No.: 589,979

[22] Filed: Sep. 28, 1990

[51] Int. Cl.$^5$ .............................................. C12N 15/12
[52] U.S. Cl. ................................. 435/172.3; 435/69.1
[58] Field of Search ..................... 435/69.1, 172.3, 244, 435/252.35

[56] References Cited

U.S. PATENT DOCUMENTS

| | | | |
|---|---|---|---|
| 4,656,132 | 4/1987 | Jean-Bassat et al. | 435/68 |
| 4,717,666 | 1/1988 | Brawner et al. | 435/253 |
| 4,745,056 | 5/1988 | Guterman et al. | 435/69.1 |
| 4,894,334 | 1/1990 | Ben-Bassat et al. | 435/69.1 |

FOREIGN PATENT DOCUMENTS 264175 8/1987 European Pat. Off. .

OTHER PUBLICATIONS

Science, 238:1704–1707, Dec. 18, 1987, Smith et al. Blocking of HIV Infectivity by a Soluble, Secreted Form of the CD4 Antigen.

J. Ferment. Tech. 66:181–185, 1988, Fujimoto et al.

C. Walsh, Enzymatic Reaction Mechanisms, published 1979, W. H. Freeman & Co., see pp. 64–67.

Michael A. Whooley, John A. O'Callaghan and Aiden J. McLoughlin, "Effect of Substrate on the Regulation of Exoprotease Production By *Pseudomonas aerugenosa* ATCC 10145", *Journal of General Microbiology*, 129(4) 981–988 (1983).

E. Strydom et al., "Detection and Characterization of Extracellular Proteases in *Butyrivibrio fibrisolvens* H17C", *Appl. Microbiol. Biotechnol*, 24:214–217 (1986).

C. Wandersman, T. Andro and Y. Bertheau, "Extracellular Proteases In *Erwinia chrysantemi*, " *Journal of General Microbiology*, 132:899–906 (1986).

C. Ratcliffe et al., "Amylase and Protease Secretion by the Marine Bacterium *Vibrio gazogenes*", A. J. Biol. Sci., 35:457–67 (1982).

S. J. Copella and Prasad Dhurjati, "α-Factor Directed Expression of the Human Epidermal Growth Factor in *Saccharomyces cerevisiae*", *Biotechnology and Bioengineering*, 33:976–83 (1989).

G. K. Whitney, B. R. Glick and C. W. Robinson, "Induction of T4 DNA Ligase in a Recombinant Strain of *E. Coli*", *Biotechnology and Bioengineering* 33:991–998 (1989).

J. Arthos, et al., "Identification of the Residues in Human CD4 Critical for the Binding of HIV", Cell, vol. 57, 469–481, May 5, 1989.

C. LaLuce and R. Molinari, "Selection Of A Chemically Defined Medium For Submerged Cultivation of *Streptomyces aureofaciens* With High Extracellular Caseinolytic Activity", *Biotechnology and Bioengineering*, vol. XIX, 1863–1884 (1977).

Werner Aretz, Klaus P. Koller and Gunther Riess, "Proteolytic Enzymes from Recombinant *Streptomyces lividans* TK24", *FEMS Microbiology Letters*, 65:31–36 (1989).

(List continued on next page.)

Primary Examiner—Robert J. Hill, Jr.
Assistant Examiner—John D. Ulm
Attorney, Agent, or Firm—Jervis, Herbert H.; Edward T. Lentz; Stuart R. Suter

[57] ABSTRACT

A method is provided for improving the yield of the heterologous proteins sCD4 and derivatives of sCD4, produced by recombinant *Streptomyces lividans* by the addition of casamino acids to the nutrient medium in which the bacteria are cultured. Also provided by this invention is a method for improving the half-life of heterologous proteins in a cell free culture supernatant by the addition of casamino acids to the supernatant. Complex media are also provided.

6 Claims, 4 Drawing Sheets

OTHER PUBLICATIONS

Philippe Dehottay et al., "Cloning And Amplified Expression in *Streptomyces lividans* Of A Gene Encoding Extracellular β-lactamase From *Streptomyces albusG*", Gene, 42:31–36 (1986).

J. R. Ludwig II, S. G. Oliver, and C. S. McLaughlin, "The Effect of Amino Acids on Growth and Phosphate Metabolism In A Prototrophic Yeast Strain", *Biochemical and Biophysical Research Communications*, vol. 79, No. 1, 16–23 (1977).

T. Erpicum et al., "Enzyme Production by Genetically Engineered Streptomyces Strains: Influence of Culture Conditions", *Biotechnology and Bioengineering*, 35:719–726 (1990).

FIG. I
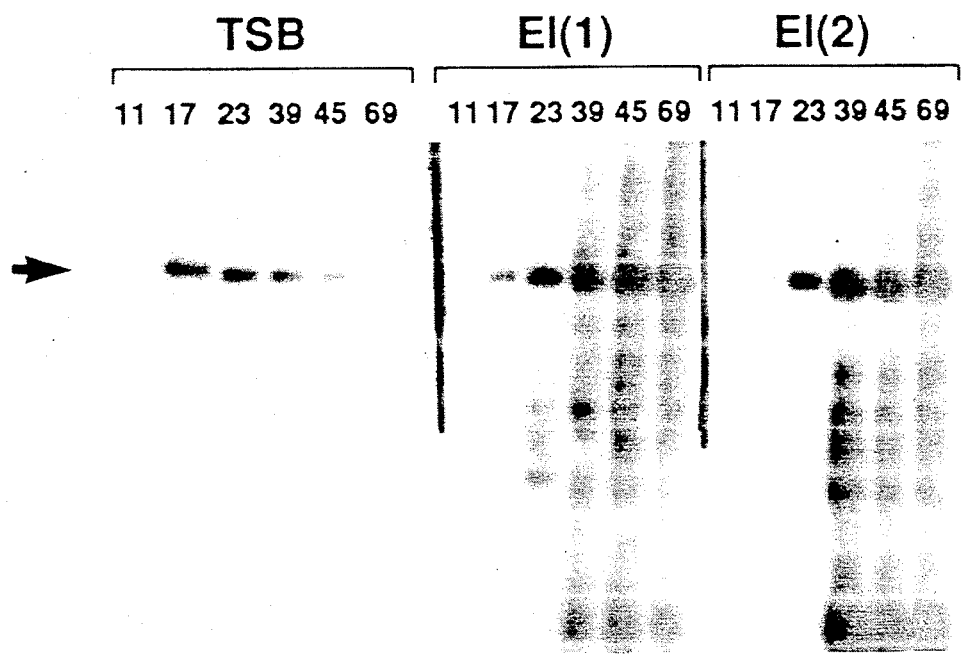
FIG. 2A
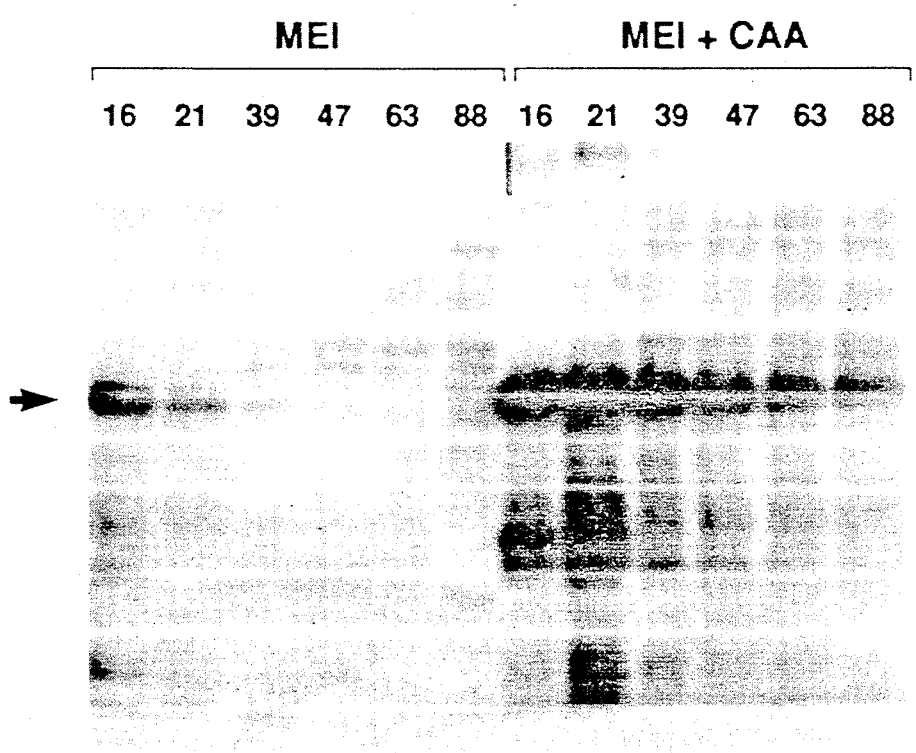

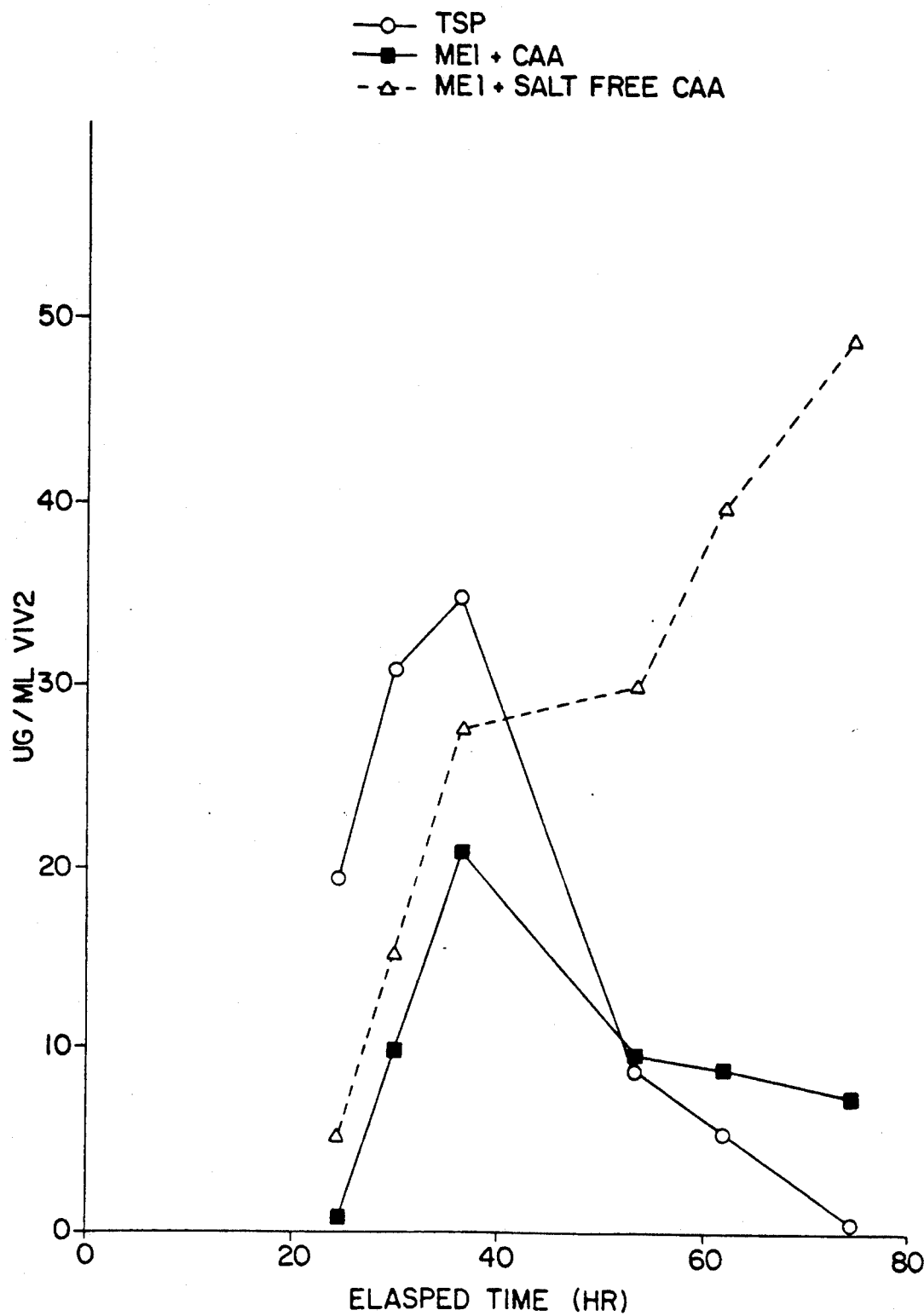

METHOD OF IMPROVING THE YIELD OF HETEROLOGOUS PROTEINS PRODUCED BY *STREPTOMYCES LIVIDANS*

FIELD OF THE INVENTION

This invention relates to a method of improving the yield and a method of improving the half-life of a heterologous protein produced from Streptomyces lividans of a heterologous protein produced from Streptomyces lividans and a complex medium.

BACKGROUND OF THE INVENTION

Streptomyces lividans has been shown to have a potential as a microbial system useful for the efficient expression of heterologous proteins. S. Chang and S. Chang, "Secretion of Heterologous Proteins in Streptomyces lividans," Biology of actinomycites, 1988, Y. Okamia, T. Bepper, and Ogawara, Eds. (Japan Scientific Societies Press, Tokyo, 1988). However, heterologous protein expression is limited in some microbial systems, such as S. lividans, because of protein instability.

In an effort to increase yields of proteins expressed and secreted by bacteria, changes in content of the fermentation media have been explored. The effects of various chemically defined medium changes on the production of extracellular proteolytic activity has been explored for non-recombinant S. aureofaciens. C. LaLuce and R. Molinari, "Selection Of A Chemically Defined Medium For Submerged Cultivation of Streptomyces aureofaciens With High Extracellular Caseinolytic Activity," Biotechnology and Bioengineering, Vol. XIX, 1863–1884 (1977). In LaLuce et al., various amino acids were used as nitrogen sources, some increasing the production of proteases while others decreased the production of proteases.

Yields of heterologous proteins expressed from recombinant strains such as S. lividans TK24, are sometimes reduced by the action of proteases. Werner Aretz, Klaus P. Koller and Gunther Riess, "Proteolytic Enzymes from Recombinant Streptomyces lividans TK24" FEMS Microbiology Letters, 65:31–36 (1989). Aretz et al. discloses the addition of metal ions to the culture medium to inhibit certain proteases thereby increasing the yield of heterologous proteins.

Other attempts to define media effects on the expression of a heterologous gene are taught by Philippe Dehottay et al., "Cloning and Amplified Expression In Streptomyces lividans Of A Gene Encoding Extracellular β-lactamase From Streptomyces albus G," Gene, 42:31–36 (1986).

Casamino acids have been used to supplement microbiological media. Casamino acids have been shown to function as a growth promotant in non-recombinant yeast when added to a medium devoid of casamino acids. J. R. Ludwig II, S. G. Oliver, and C. S. McLaughlin, "The Effect Of Amino Acids On Growth And Phosphate Metabolism In A Prototrophic Yeast Strain," Biochemical and Biophysical Research Communications, Vol. 79, No. 1, 16–23 (1977).

A repressive effect of casamino acids has been demonstrated on exoprotease production in early phases of fermentation of Pseudomonas aerugenose. Michael A. Whooley, John. A. O'Callaghan and Aiden J. McLoughlin, "Effect Of Substrate On The Regulation Of Exoprotease Production By Pseudomonas aerugenosa ATCC 10145, " Journal Of General Microbiology, 129(4) 981–988 (1983).

In comparison, E. Strydom et al., in "Detection And Characterization Of Extracellular Proteases in Butyrivibrio fibrisolvens H17C," Appl. Microbiol. Biotechnol, 24:214–217 (1986) demonstrated protease production was maximal on a medium with casamino acids. Similarly, a tryptic digest of casein was shown to increase proteolytic activity in E. chrysanteoni. C. Wanderman, T. Andro and Y. Bertheau, "Extracellular Proteases in Erwinia chrysantemi," Journal of General Microbiology, 132:899–906 (1986). Additionally, casamino acids added to a complete medium increased protease production from Vibrio gazogenes. C. Ratcliffe et al. "Amylase and Protease Secretion By The Marine Bacterium Vibrio gazogenes," A.J. Biol. Sci., 35:457–67 (1982).

A variety of complex medium formulations, some including casamino acids, improved product production from recombinant yeast. S. J. Copella and Prasad Dhurjati, "α-Factor Directed Expression Of The Human Epidermal Growth Factor In Saccharomyces cerevisiae," Biotechnology and Bioengineering, 33:976–83 (1989). The addition of the combination, glucose and casamino acids to a totally defined medium where E. coli must synthesize, among others, amino acids, vitamins and nucleotides, increased the production level of a heterologous protein. G. K. Whitney, B. R. Glick and C. W. Robinson, "Induction of T4 DNA Ligase In A Recombinant Strain Of E. Coli, " Biotechnology and Bioengineering 33:991–998 (1989). During the terminal phase of cultivation, the addition of a water soluble alcohol and/or amino acid mixture has been demonstrated to improve the yield of a heterologous protein such as IFN-alpha, IFN-beta and IL-2 produced by recombinant bacteria. U.S. Pat. No. 4,656,132.

Casamino acids have also been shown to decrease the yield of a recombinant protein in a strain of Streptomyces. T. Erpicum et al., "Enzyme Production by Genetically Engineered Streptomyces Strains: Influence of Culture Conditions," Biotechnology and Bioengineering, 35:719–726 (1990).

SUMMARY OF THE INVENTION

This invention lies in the discovery of a method for improving the yield of heterologous proteins produced by cultivating recombinant Streptomyces lividans in a liquid nutrient medium comprising the addition of an effective amount of casamino acids to the medium.

This invention further lies in the discovery of a complex medium comprising glucose, soy peptone, yeast extract, $CaCO_3$ and $CoCl_2$. Preferably, the media may be supplemented with an effective amount of casamino acids.

This invention further lies in the discovery of a method of improving the half-life of heterologous proteins in a substantially cell-free culture supernatant, said heterologous proteins produced by cultivating recombinant Streptomyces lividans, comprising the addition of an effective amount of casamino acids to the supernatant.

BRIEF DESCRIPTION OF THE DRAWINGS

FIG. 1 is a photography of a gel demonstrating increased extracellular levels of sCD4 in E1 medium with calcium carbonate (1) and E1 medium without calcium carbonate (2) versus TSB. The gel depicts 11 to 69 hours into fermentation.

FIG. 5 is a graph of time versus concentration of V1V2 in TSB alone, ME1+5% CAA and ME1+5% Salt-Free CAA..

DETAILED DESCRIPTION OF THE INVENTION

Figure 2B:
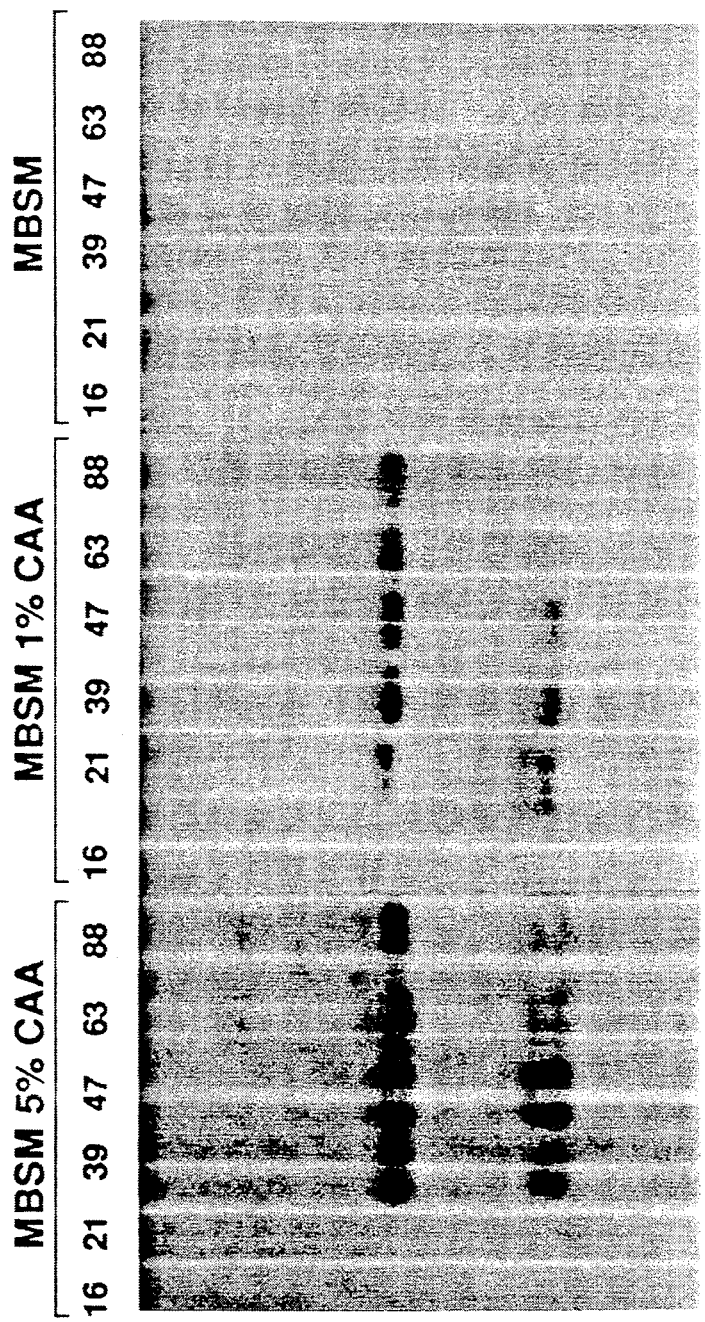
FIGS. 2(a) & (b) are photographs of gels demonstrating extracellular accumulation of sCD4 in E1 alone and E1+5% CAA, in MBSM+1% CAA and MBSM+5% CAA. Hours into fermentation are shown at the top of the gels.

The term "heterologous" as used herein refers to polypeptides not produced by the wild type bacteria S. lividans. The heterologous peptides sCD4 and derivatives of sCD4 are preferred in this invention.

A cDNA sequence of the human CD-4 receptor has been described (Maddon, et al., Cell 43:93 (1985)). The complete CD-4 pre-protein sequence is 458 amino acids in length comprising the putative 23 amino acid secretory leader, 372 amino acid surface ($V_1$–$V_4$), 23 amino acid transmembrane and 40 amino acid cytoplasmic domains. sCD4 is a soluble derivative of CD-4 which lacks the transmembrane and cytoplasmic domains of CD-4.

The term "derivative of sCD4" as used herein refers to derivatives as defined in commonly owned copending U.S. patent application Ser. No. 07/160,463, filed Feb. 24, 1988, now abandoned, which is incorporated by reference as if fully set forth herein. See also Arthos et al., "Identification of the Residues in Human CD4 Critical for the Binding of HIV," *Cell*, 57:469–81 (1989). Generally, such derivatives comprise additions, deletions or substitutions which alterations do not significantly adversely affect secretion of the protein into the conditioned medium and the affinity of the protein for HIV env protein, i.e., gp120. For example, one or a few amino acids can be added to, or deleted from, the N- or C-terminus. Or, one or a few amino acids, preferably no more than four amino acids can be inserted into, deleted or substituted for internal amino acids. Alternatively, a hybrid protein, i.e., a translational fusion, can be constructed between sCD4 and a protein carrier, another antigen or other sCD4 molecules to prepare a poly-sCD4 molecule. In yet another alternative, sCD4 can be synthetically conjugated to a carrier molecule.

Derivatives of sCD4include, but are not limited to, V1V2 and V1J4. V1J4 has amino acids (−)2-104 (N-glutamine-glycine-lysine-through-alanine-asparagine-serine-C) fused to amino acids 351–369 (-glycine-glutamine-valine-through-threonine-proline-valine-C).

V1V2 has amino acids 1-183(N-lysine-lysine-valine-through lysine-alanine-serine-C). Copending U.S. patent application Ser. No. 07/160,463, filed Feb. 24, 1988, now abandoned, describes one method for the expression of sCD4 proteins by *Streptomyces lividans*. Generally, these fusions utilize the LTI (See EP-A-264,175 published Apr. 20, 1988) and Bgal (Eckhardt, et al., *J. Bacteriol*, 169:4249–4256 (1987)) and Brawner, et al., (U.S. Pat. No. 4,717,666) signal sequences to direct sCD4 secretion into the culture supernatant. The sCD4 coding sequence is fused at a site within the coding region of the mature LTI or Bgal protein to preserve the signal sequence cleavage site which is expected to ensure accurate processing and secretion of the sCD4 fusion proteins. Any method by which sCD4 and derivatives thereof are expressed by *S. lividans* is expected to be useful in this invention.

The recombinant bacteria, *Streptomyces lividans*, used in this invention may be made by known recombinant DNA techniques. These techniques typically involve (1) cloning a synthetic structural gene or a structural gene of genomic origin that encodes the heterologous polypeptide into an appropriate plasmid or viral expression vector at a site which permits expression thereof, (2) introducing the vector into competent bacteria, and (3) selecting recombinant cells (also called "transformants") either by a plasmid marker function or their ability to produce the heterologous polypeptide.

A DNA coding sequence and amino acid sequence of sCD4 are illustrated below.

```
          !0                         30                         50
CAAGCCCAGAGCCCTGCCATTTCTGTGGGCTCAGGTCCCTACTGCTCAGCCCCTTCCTCC

70                        ·90                        110
CTCGGCAAGGCCACAATGAACCGGGGAGTCCCTTTTAGGCACTTGCTTCTGGTGCTGCAA
                  Met Asn Arg Gly Val Pro Phe Arg His Leu Leu Leu Val Leu Gln 130                        150                        170
CTGGCGCTCCTCCCAGCAGCCACTCAGGGAAAGAAAGTGGTGCtGGGCAAAAAAGGGGAT
Leu Ala Leu Leu Pro Ala Ala Thr Gln Gly Lys Lys Val Val LeuGly Lys Lys Gly Asp
    −9                                −1  +1

190                        210                        230
ACAGTGGAACTGACCTGTACAGCTTCCCAGAAGAAGAGCATACAATTCCACTGGAAAAAC
Thr Val Glu Leu Thr Cys Thr Ala Ser Gln Lys Lys Ser Ile Gln Phe His Trp Lys Asn 250                        270                        290
TCCAACCAGATAAAGATTCTGGGAAATCAGGGCTCCTTCTTAACTAAAGGTCCATCCAAG
Ser Asn Gln Ile Lys Ile Leu Gly Asn Gln Gly Ser Phe Leu Thr Lys Gly Pro Ser Lys 310                        330                        350
CTGAATGATCGCGCTGACTCAAGAAGAAGCCTTTGGGACCAAGGAAACTTCCCCCTGATC
Leu Asn Asp Arg Ala Asp Ser Arg Arg Ser Leu Trp Asp Gln Gly Asn Phe Pro Leu Ile 370                        390                        410
ATCAAGAATCTTAAGATAGAAGACTCAGATACTTACATCTGTGAAGTGGAGGACCAGAAG
Ile Lys Asn Leu Lys Ile Glu Asp Ser Asp Thr Tyr Ile Cys Glu Val Glu Asp Gln Lys
```

-continued

```
          430                     450                       470
GAGGAGGTGCAATTGCTAGTGTTCGGATTGACTGCCAACTCTGACACCCACCTGCTTCAG
Glu Glu Val Gln Leu Leu Val Phe Gly Leu Thr Ala Asn Ser Asp Thr His Leu Leu Gln
                                                      104

490                     510                       530
GGGCAGAGCCTGACCCTGACCTTGGAGAGCCCCCCTGGTAGTAGCCCCTCAGTGCAATGT
Gly Gln Ser Leu Thr Leu Thr Leu Glu Ser Pro Pro Gly Ser Ser Pro Ser Val Gln Cys 550                     570                       590
AGGAGTCCAAGGGGTAAAAACATACAGGGGGGGAAGACCCTCTCCGTGTCTCAGCTGGAG
Arg Ser Pro Arg Gly Lys Asn Ile Gln Gly Gly Lys Thr Leu Ser Val Ser Gln Leu Glu 610                     630                       650
CTCCAGGATAGTGGCACCTGGACATGCACTGTCTTGCAGAACCAGAAGAAGGTGGAGTTC
Leu Gln Asp Ser Gly Thr Trp Thr Cys Thr Val Leu Gln Asn Gln Lys Lys Val Glu Phe
151

670                     690                       710
AAAaTAGACATCGTGGTGCTAGCTTTCCAGAAGGCCTCCAGCATAGTCTATAAGAAAGAG
Lys Ile Asp Ile Val Val Leu Ala Phe Gly Lys Ala Ser Ser Ile Val Tyr Lys Lys Glu
                                                      183

730                     750                       770
GGGGAACAGGTGGAGTTCTCCTTCCCACTCGCCTTTACAGTTGAAAAGCTGACGGGCAGT
Gly Glu Gln Val Glu Phe Ser Phe Pro Leu Ala Phe Thr Val Glu Lys Leu Thr Gly Ser 790                     810                       830
GGCGAGCTGTGGTGGCAGGCGGAGAGGGCTTCCTCCTCCAAGTCTTGGATCACCTTTGAC
Gly Glu Leu Trp Trp Gln Ala Glu Arg Ala Ser Ser Ser Lys Ser Trp Ile Thr Phe Asp 850                     870                       890
CTGAAGAACAAGGAAGTGTCTGTAAAACGGGTTACCCAGGACCCTAAGCTCCAGATGGGC
Leu Lys Asn Lys Glu Val Ser Val Lys Arg Val Thr Gln Asp Pro Lys Leu Gln Met Gly 910                     930                       950
AAGAAGCTCCCGCTCCACCTCACCCTGCCCCAGGCCTTGCCTCAGTATGCTGGCTCTGGA
Lys Lys Leu Pro Leu His Leu Thr Leu Pro Gln Ala Leu Pro Gln Tyr Ala Gly Ser Gly 970                     990                       1010
AACCTCACCCTGGCCCTTGAAGCGAAAACAGGAAAGTTGCATCAGGAAGTGAaCCTGGTG
Asn Leu Thr Leu Ala Leu Gly Ala Lys Thr Gly Lys Leu His Gln Glu Val Asn Leu Val 1030                    1050                      1070
GTGATGAGAGCCACTCAGCTCCAGAAAAATTTGACCTGTGAGGTGTGGGGACCCACCTCC
Val Met Arg Ala Thr Gln Leu Gln Lys Asn Leu Thr Cys Glu Val Trp Gly Pro Thr Ser 1090                    1110                      1130
CCTAAGCTGATGCTGAGCTTGAAACTGGAGAACAAGGAGGCAAAGGTCTCGAAGCGGGAG
Pro Lys Leu Met Leu Ser Leu Lys Leu Glu Asn Lys Glu Ala Lys Val Ser Lys Arg Glu 1150                    1170                      1190
AAGGCGGTGTGGGTGCTGAACCCTGAGGCGGGGATGTGGCAGTGTCTGCTGAgTGACTCG
Lys Ala Val Trp Val Leu Asn Pro Glu Ala Gly Met Trp Gln Cys Leu Leu Ser Asp Ser 1210                    1230                      1250
GGACAGGTCCTGCTGGAATCCAACATCAAGGTTCTGCCCACATGGTCCACCCCGGtgtaa
Gly Gln Val Leu Leu Glu Ser Asn Ile Lys Val Leu Pro Thr Trp Ser Thr Pro Val End
351                                                                         369

1270
tggcgcctctaga
```

The heterologous protein-producing *Streptomyces lividans* are then cultured in a liquid nutrient medium. The liquid nutrient medium is generally comprised of an excess of conventional nutrient materials that fulfill the cellular growth requirements of *Streptomyces lividans*. The materials include sources of carbon and nitrogen for synthesis of cellular components and energy, and minerals (ions), examples include sulfur, phosphorous, magnesium, potassium, iron. One or more amino acids may be added to the media. The liquid nutrient medium may be a defined or complex medium.

Preferred liquid nutrient media for use in this invention are the complex media. Particularly preferred for improving the yield or half-life of heterologous proteins is a complex medium of the formula:

(a) about 20 to about 30 grams per liter glucose;
(b) about 20 to about 50 grams per liter soy peptone;
(c) about 1 grams per liter yeast extract;
(d) about 0 to about 1 grams per liter $CaCO_3$; and
(e) about 1 mg per liter $CoCl_2$.

The term "casamino acids" (CAA) as used herein refers to the acid hydrolysate of casein. An effective amount of CAA added to the medium to improve the yield or half-life of heterologous proteins is in the range from about 1% to about 5% (w/v). Additionally, the CAA can be salt-free (SF CAA). The upper limit on CAA is governed by economics and an undesirable inhibition of cellular growth.

Soluble CD4 and derivatives of sCD4 are secreted by *Streptomyces lividans* into the culture supernatant. As a first step in the protein recovery process, a clarified culture supernatant is prepared by centrifugation. The sCD4 and derivatives can then by purified by a combination of affinity chromatography, gel filtration or other protein purification processes.

Further provided by this invention is a method of improving the half-life of heterologous proteins in a substantially cell-free culture supernatant, said heterologous proteins produced by cultivating recombinant *S. lividans*, comprising the addition of from about 1 to about 5% (w/v) casamino acids to the supernatant. Preferred heterologous proteins are sCD4 and derivatives of sCD4 as detailed herein.

EXAMPLES

Materials and Methods

Bacterial Strains and Plasmids

*Streptomyces lividans* 1326 (Bibb, et al., *Mol Gen Genet* 184:230 (1981)) was used in all the examples described below. Plasmids used to express sCD4 and derivatives of sCD4 contained a sCD4 minigene (U.S. patent application Ser. No. 07/160,463, filed Feb. 24, 1988, now abandoned, operatively linked to the *Streptomyces longisporus* trypsin inhibitor (LTI) promoter and signal sequence (EP-A-264,175, published Apr. 20, 1988), as well as Streptomyces plasmid replication functions as found plasmids pIJ350 and pIJ351 (Keiser, et al., *Mol Gen Genet* 185:223 (1982)). Plasmid pLTI:sT4/7 (U.S. Ser. No. 160,463, filed Feb. 24, 1988, now abandoned) was used for expression of sCD4.

V1J4 expression was directed by plasmid pLTI/V1J4 which was prepared substantially as described for pLTI:sT4/7.

The parental plasmid used for V1V2 was 12B1 was constructed as follows: The BbvI cleavage site within the coding sequence for the CD4 signal peptide (between nucleotides 148 and 149 of the CD4 DNA sequence; Maddon, et al., *Cell* 42:93-104 (1985)) was moved by site directed mutagenesis (Kunkel, *Proc. Natl. Acad. Sci. USA* 82:488-492)) such that the BbvI cleavage site was placed between nucleotides 150 and 151. This mutation (#1478) was inserted into a sCD4 minigene which contained the coding sequence for amino acid residues 1-129. An EcoRI+HindIII fragment containing the 1478 mutation was transferred from M13mp18 into pUC18 to generate pUCV1pV2(1478). Following BbvI digestion of pUCV1pV2(1478) it was treated with the Klenow fragment of DNA polymerase I to fill-in the 5' single-stranded sequence, then digested with HindIII. The HindIII-blunt end fragment resulting from these manipulations was cloned into pLTI450 (U.S. Ser. No. 07/160,463 filed Feb. 24, 1988, now abandoned) which had been digested with AccI, treated with DNA polymerase I Klenow fragment and digested with HindIII. The resulting plasmid, 12B1/1477, contains a sCD4 minigene (amino acid residues 1-129) fused to the coding sequence of the LTI signal sequence such that the expressed V1V2 protein will contain at its amino terminus the 6 amino acid LTI pro peptide plus residues 1 and 2 of the mature LTI protein. A Streptomyces replicon and selectable marker were cloned into 12B1/1477 by inserting pIJ351 (Kieser, et al., *Mol. Gen. Genet.* 185:223-238 (1982) using the unique PstI site within both plasmids. To create a complete V1V2 minigene (amino acid residues 1-183) within the 12B1/1477 context an AflIII+XbaI fragment from DHFR V1V2 183#7 was inserted into 12B1/1477 which had been digested with AflIII and XbaI. The resulting plasmid was 12B1.

These plasmids described above were transformed into *Streptomyces lividans* using standard procedures (see Hopwood, et al., Genetic Manipulation of Streptomyces—A Laboratory Manual, F. Crowe & Sons, Ltd., Norwich, England (1985)). Transformants were selected by overlaying the transformation plates with 0.4% agar containing 100 μg/ml thiostrepton.

sCD4 quantitation by Immunoblotting

Cell free supernatants and purified sCD4 were separated on 10% or 12.5% polyacrylamide (30:0.8 acrylamide:bis)sodium dodecyl sulfate gels (Laemmli, *Nature* 227:680-685 (1970)), then transferred to nitrocellulose (Towbin, et al., *Proc. Natl. Acad. Sci. USA* 76:4350-4354 (1979)). The nitrocellulose filter was processed to detect sCD4 (Brawner, et al., *Gene* 40:191-201 (1985)) using rabbit anti-serum prepared against sCD4. The bound antibody was detected with $^{125}$I-protein A. Bound $^{125}$I-protein A (which is proportional to the amount of sCD4 present on the nitrocellulose filter) was quantitated using an Ambis radioanalytic imaging system. The sCD4 concentration for the experimental samples was determined by including known sCD4 concentrations on each immunoblot.

| Media Ingredient | Concentration (g/L batched vol.) |
|---|---|
| (1) TSB | |
| Pancreatic Digest of Casein (CAA) | 17 |
| Papaic digest of soy meal | 3 |
| NaCl | 5 |
| K$_2$HPO$_4$ | 2.5 |
| Dextrose | 2.5 |
| H$_2$O Source: (deionized) DI | |
| (2) MBSM | |
| L-Asparagine | 2 |
| MgCl$_2$.6H$_2$O | 0.5 |
| CaCl$_2$.2H$_2$O | 0.01 |
| NaCl | 1 |
| K$_2$HPO$_4$ | 3 |
| KH$_2$PO$_4$ | 0.5 |
| FeCl$_2$.6H$_2$O | 1 mg/L |
| (NH$_4$)$_2$SO$_4$ | 30 |
| H$_2$O Source: DI | |
| pH Adjustment: 7.0-7.2 | |
| Additives: glucose added to 3% final concentration after sterilization. | |
| (3) E1 | |
| Glucose | 20 |
| Soy Peptone | 20 |
| Yeast Extract | 1 |
| CaCO$_3$ | 1 |
| CoCl$_3$ | 1 mg/L |
| H$_2$O Source: DI | |
| (4) ME1 | |
| Glucose | 30 |
| Soy peptone | 50 |
| Yeast Extract | 1 |
| CaCo$_3$ | 1 |
| CoCl$_2$ | 1 mg/L |
| H$_2$O Source: DI | |
| pH Adjustment: None | |

EXAMPLE 1

Effect of casamino acids on the half-life of sCD4

Seed cultures for the sCD4 producing *Streptomyces lividans* strain were prepared by inoculating 50 ml of TSB containing 5 μg/ml thiostrepton with 5 mg (dry cell weight or DCW) of frozen mycelia. The seed culture was grown at 28° C. for 30-34 hours using a Variomag Electronicruhrer multipoint HP stir plate. The mycelia were harvested by a 5 minute centrifugation in a Beckman TJ-6 centrifuge and then used as the inoculum for either a TSB or TSBB +5% casamino acids fermentation. These shake flask fermentations were inoculated to an initial biomass of 1 gram cell (DCW) per liter of culture, with a final volume of 200 ml in a 2L. Erlenmeyer flask. Thiostrepton was added to each fermentation flask to a final concentration of 5 μg/ml. The cultures were shaken (300 rpm) at 28° C. on a New Brunswick Scientific G10 gyratory shaker.

At specific times during the growth period, cell free supernatant was prepared by centrifugation as described above. One hundred ml of cell free supernatant was transferred to a 2L. Erlenmeyer flask and shaken at 28° C. A sample was taken every hour for 4 hours, beginning at t=0 hour. The concentration of sCD4 present at each time point was quantitated by immunoblotting as described above. The rate of sCD4 disappearance is equal to the slope of the lop [sCD4] versus time relationship. The sCD4 half life was calculated using the following equations.

$$\ln(X/Xo) = rt \quad (1)$$

where r = rate of disappearance $$\ln(0.5Xo/Xo) = rt \quad (2)$$

$$t1/2 = -0.693/r \quad (3)$$

Results: The results of the sCD4 half-life experiments are summarized in Table 1. At the earliest time point assayed (6 hours), sCD4 stability as reflected in half-life values was approximately the same for both fermentation media tested (TSB or TSB+5% CAA). This trend, however, was not noted at subsequent time points. At all other time points, sCD4 half-life was significantly decreased in TSB fermentations when compared to the half-life value noted for the comparable TSB+5% CAA fermentation. Only at the latest time point (36 hours) did the half-life value for the TSB+5% CAA fermentation (4.6 hours) approximate the value noted in the comparable TSB fermentation (2.9 hours).

Conclusion: The results of the studies indicate that the stability of sCD4 is specifically enhanced by the inclusion of casamino acids to the growth medium.

TABLE 1

| Half-Life of sCD4 in TSB +/− 5% Casamino acids Fermentations[1] | | |
|---|---|---|
| Time of Fermentation | TSB | TSB + 5% CAA |
| 6 hr | 5.1 hr | 5.7 hr |
| 9 hr | 6.2 hr | 14.7 hr |
| 12 hr | 4.5 hr | 19.8 hr |
| 24 hr | 4.1 hr | 13.1 hr |
| 36 hr | 2.9 hr | 4.6 hr |

[1]Experimental samples were taken every hour for four hours.

EXAMPLES 2-6

Examples 2-6 demonstrate the development of improved media for production of sCD4-related molecules in *S. lividans*. These examples show production results for sCD4 and two derivaties in different media in 10L fermentations. Examples 2-6 demonstrate the superiority of E1 and ME1, novel media described herein, over TSB for improving the yield of sCD4. These examples also demonstrate that the addition of CAA to either defined or complex media results in an increase in the peak yield levels of several sCD4-related proteins.

Preparation of Seed Cultures

All 10L fermentations for these Examples were inoculated from shake flask seeds grown in 1L of Trypticase Soy Broth (TSB) or MBSM (with 5 μg/ml thiostrepton) in 2.8L Fernbach flasks shake at 170rpm at 28° C. for 24 to 48 hours.

Protocol for Examples Performed at 10L Scale

All 10L scale studies were performed in 15L, Biolafitte fermentors containing approximately 10L of medium. The temperature, back pressure, and aeration rate were controlled at 28° C. 7 PSIG, and 5 standard liters per minute (SLPM) respectively. PH was controlled at 7.0 using NaOH and phorphoric acid except where otherwise indicated. The agitation rate was initially set at 300 RPM. Following inoculation, the dissolved oxygen (DO) was allowed to fall to 20% saturation; the DO was then automatically controlled at 20% by a proporational integral derivative (PID) algorithm which coupled the agitation to the DO concentration. Thiostrepton was added to a final concentration of 5 μg/ml.

Source of Casamino Acids

Difco casamino acids were used in all experiments, except where indicated.

EXAMPLE 2

Accumulation of sCD4 in Cultures of *Streptomyces lividans* Grown in E1, E1 Without Calcium carbonate and TSB was demonstrated Protocol: A 10L scale experimental control was conducted as described above in TSB, E1 with calcium carbonate (1) and E1 without calcium carbonate (2).

Results: Extracellular levels of sCD4 were higher in E1 medium than in TSB medium. (Note: both TSB and E1 are considered complex). Furthermore, sCD4 levels in TSB declined rapidly after the production peak at 17 hours into fermentation, whereas production levels remained relatively constant over a 30 hour period in E1. (FIG. 1).

EXAMPLE 3

Effect of Casamino Acids on the Extracellular Accumulation of sCD4 in Complex and Defined Media Protocol: In this 10L experiment, extracellular accumulation of sCD4 was monitored in complex (E1) and defined (MBSM) media with and without the addition of CAA. Five media were used: (1) E1; (2) E1+5% CAA; (3) MBSM; (4) MBSM+1% CAA; and (5) MBSM+5% CAA.

Results of Western Blot Analysis: In complex (E1) medium, the addition of CAA resulted in increased accumulation of sCD4 over that observed in E1 without CAA. In MBSM, no extracellular accumulation of sCD4 was observed unless CAA was added. Also, extracellular accumulation of sCD4 was greater in MBSM+5% CAA than in MBSM+1% CAA. (FIGS. 2(a) & (b)).

EXAMPLE 4

Figure 3:
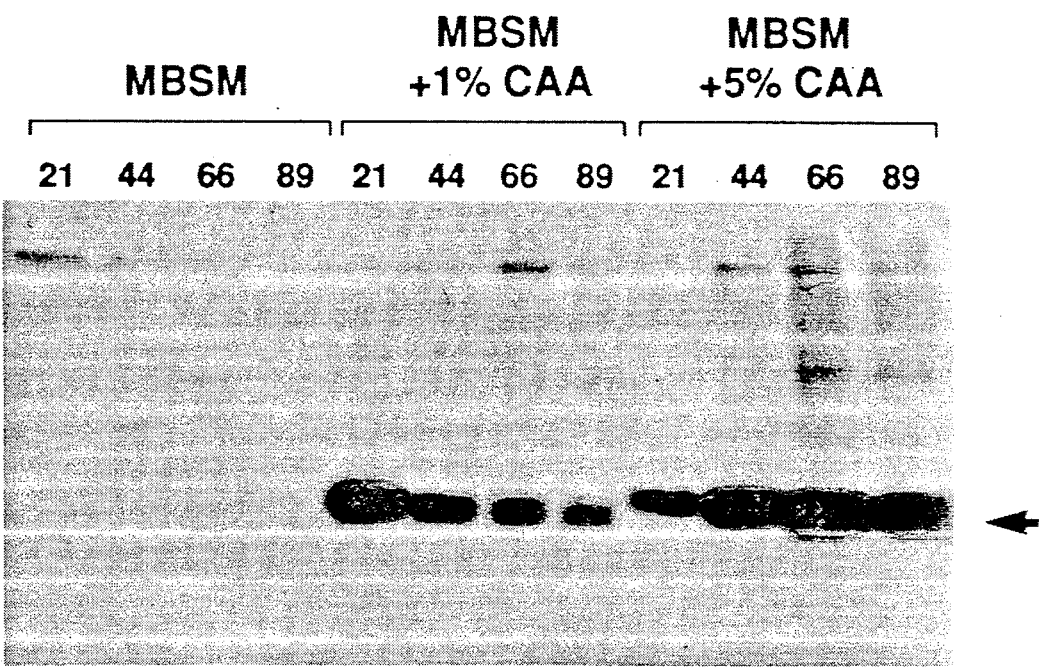
FIG. 3 is a photograph of a gel depicting the lack of extracellular accumulation of V1J4 MBSM alone and extracellular accumulation of V1J4 when 1% and 5% CAA were added to MBSM. The gel depicts 21 to 89 hours into fermentation.

Extracellular Accumulation of V1J4 by S. Lividans Gown in Defined Medium (MSBM) with 0, 1, or 5% CAA Results of Western Blot Analysis: No extracellular accumulation of V1J4 was observed in MBSM alone. Extracellular accumulation of V1J4 in MBSM+1% CAA was highest in the sample taken 21 hours after inoculation, and declined thereafter. In MBSM+5% CAA as defined previously, V1J4 accumulation peaked between 44 and 89 hours after inoculation, and appeared to remain fairly constant throughout that period. (FIG. 3).

EXAMPLE 5

Figure 4:
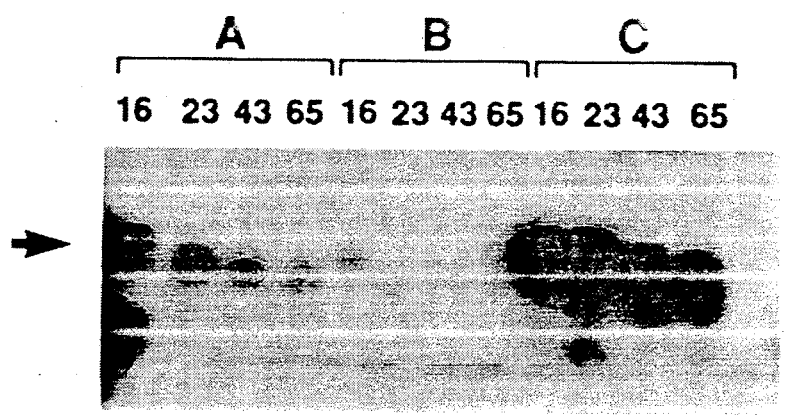
FIG. 4 is a photograph of a gel depicting higher extracellular accumulation of V1J4 in E1+5% CAA (C) than in either TSB (A) or E1 alone (B). The gel depicts 16 to 65 hours into fermentation.

Accumulation of V1J4 in cultures of S. Lividans Gown in Trypticase Soy Broth (TSB), E1, and E1+5% CAA Results of Western Blot Analysis: In TSB (A in FIG. 4) as defined previously, peak extracellular accumulation of V1J4 was observed 16 hours after inoculation, and declined rapidly thereafter. In E1 (B in FIG. 4) as described previously, extracellular accumulation of V1J4 was much lower than that observed in TSB; as in TSB, peak accumulation was observed 16 hours after inoculation, with a rapid decline in V1J4 titers after that point. In E1+5% CAA (C in FIG. 4), extracellular accumulation of V1J4 was much higher than in either TSB or E1. (FIG. 4).

EXAMPLE 6

Extracellular Accumulation of V1V2 in TSB, ME1+5% Difco CAA, and ME1+5% HYCASE SF (Salt Free Casamino Acids from Sheffield Products)

Protocol: V1V2 accumulation was quantitated using an AMBIS radio image analyzer.

Results: Accumulation of V1V2 was highest in ME1+SF CAA (approximately 50 mg/ml). In TSB, V1V2 levels peaked at about 35 μg/ml, and in ME1+- Difco CAA, peak accumulation was 21 μg/ml. (FIG. 5).

In summary, Examples 2-6 demonstrate that E1 is a superior medium to TSB for improving the yield of sCD4. However, the medium E1+5%CAA (or the closely related ME1+5% CAA) is superior to both TSB and E1 (or ME1) for improving the yield of both sCD4 and V1. Furthermore, the addition of CAA to the defined medium MBSM significantly improved the yield of sCD4 derivative. Thus, the addition of CAA had a significant positive effect on the yield of heterologous proteins produced by S. lividans.

EXAMPLE 7

Casamino acids prolong the half life of sCD4 produced by S. lividans

Protocol: Following the sCD4 half-life procedure described in Example 1, the half-life of sCD4 was determined when CAA were added to a cell-free culture supernatant at the conclusion of three TSB fermentations without CAA. Culture supernatants were harvested after 6, 12 and 24 hours growth. These time points were chosen because they are representative samples of extracellular proteins present during the active growth phase (6 hours), the entry into stationary phase (12 hours) and stationary phase (24 hours). The cells were removed by centrifugation to prepare a cell free supernatant for the half-life studies. A casamino acids solution (5% final concentration) was added to one half of the cell-free supernatant. Samples from the cell-free supernatant were taken for sCD4 quantitation after 0, 30, 60, 90 and 120 minutes incubation at 28° C. sCD4 was quantitated from an immunoblot using an Ambis radioanalytic imaging system.

Results: As summarized in Table II, the sCD4 half-life after 12 and 24 hours fermentation was significantly increased when a casamino acids solution was added to the cell-free supernatant. In contrast, casamino acids did not have any detectable effect on the sCD4 half-life after 6 hours of growth.

TABLE II

| Time within growth cycle (hr) | sCD4 half-life (hr) | |
|---|---|---|
| | − casamino acids | + casamino acids |
| 6 | 3 | 4.3 |
| 12 | 3 | >20 |
| 24 | 2 | >20 |

What is claimed is:

1. A method of improving the yield of heterologous proteins selected from the group consisting of sCD4 and derivatives of sCD4, said method comprising cultivating recombinant *Streptomyces lividans* in a liquid nutrient medium comprising:
   (a) about 20 to about 30 grams per liter glucose;
   (b) about 20 to about 50 grams per liter soy peptone;
   (c) about 1 grams per liter yeast extract;
   (d) about 0 to about 1 gram per liter $CaCO_3$;
   (e) about 1 mg per liter $CoCl_2$ and
   (f) about 1 to about 5% (w/v) casamino acids.

2. The method of claim 1 wherein the derivative is V1J4.

3. The method of claim 1 wherein the derivative is V1V2.

4. A method of improving the half-life of heterologous proteins in a substantially cell-free culture supernatant, said heterologous proteins selected from the group consisting of sCD4 and derivatives of sCD4 produced by cultivating recombinant *Streptomyces lividans* comprising the addition of from about 1 to about 5% (w/v) casamino acids to the supernatant wherein the supernatant comprises:
   (a) about 20 to about 30 grams per liter glucose;
   (b) about 20 to about 50 grams per liter soy peptone;
   (c) about 1 gram per liter yeast extract;
   (d) about 0 to about 1 gram per liter $CaCO_3$; and
   (e) about 1 mg per liter $CoCl_2$.

5. The method of claim 4 wherein the derivative is V1J4.

6. The method of claim 4 wherein the derivative is V1V2.